(12) United States Patent
Tockman et al.

(10) Patent No.: US 7,239,923 B1
(45) Date of Patent: Jul. 3, 2007

(54) LEAD HAVING VARYING STIFFNESS AND METHOD OF MANUFACTURING THEREOF

(75) Inventors: Bruce Tockman, Scandia, MN (US); Randy Westlund, Minneapolis, MN (US); Gwen Crevensten, Minneapolis, MN (US); Lili Liu, White Bear Lake, MN (US); Chris Zerby, New Brighton, MN (US); Jay A. Warren, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 998 days.

(21) Appl. No.: 09/630,000

(22) Filed: Aug. 1, 2000

(51) Int. Cl.
*A61N 1/05* (2006.01)

(52) U.S. Cl. ...................... 607/119; 600/373

(58) Field of Classification Search ........ 600/372–375, 600/377, 382, 384; 607/119, 122, 125
See application file for complete search history.

(56) References Cited

U.S. PATENT DOCUMENTS

| | | | |
|---|---|---|---|
| 4,437,474 A | 3/1984 | Peers-Trevarton | 128/781 |
| 4,458,695 A | 7/1984 | Peers-Trevarton | 128/786 |
| 4,640,983 A * | 2/1987 | Comte | 174/119 R |
| 4,651,751 A | 3/1987 | Swendson et al. | 128/786 |
| 4,938,822 A | 7/1990 | Peers-Trevarton | 156/144 |
| 5,007,435 A | 4/1991 | Doan et al. | 128/784 |
| 5,052,407 A * | 10/1991 | Hauser et al. | 607/125 |
| 5,115,818 A | 5/1992 | Holleman et al. | 128/784 |
| 5,251,643 A | 10/1993 | Osypka | 607/122 |
| 5,257,634 A | 11/1993 | Kroll | 607/122 |
| 5,354,327 A | 10/1994 | Smits | 607/116 |
| 5,383,852 A | 1/1995 | Stevens-Wright | 604/95 |
| 5,456,707 A | 10/1995 | Giele | 607/127 |
| 5,476,500 A | 12/1995 | Fain et al. | 607/126 |
| 5,524,338 A | 6/1996 | Martynink et al. | 29/825 |
| 5,566,672 A | 10/1996 | Faasse, Jr. | 128/640 |
| 5,639,276 A | 6/1997 | Weinstock et al. | 606/129 |
| 5,683,445 A | 11/1997 | Swoyer | 607/125 |
| 5,716,391 A | 2/1998 | Grandjean | 607/127 |
| 5,849,032 A * | 12/1998 | Van Venrooij | 607/123 |
| 5,935,159 A * | 8/1999 | Cross et al. | 607/116 |
| 5,995,876 A * | 11/1999 | Kruse et al. | 600/374 |
| 6,070,104 A | 5/2000 | Hine et al. | 607/123 |

(Continued)

FOREIGN PATENT DOCUMENTS

DE 20010369 9/2000

(Continued)

*Primary Examiner*—George R. Evanisko
(74) *Attorney, Agent, or Firm*—Schwegman, Lundberg, Woessner & Kluth, P.A.

(57) ABSTRACT

An apparatus includes a lead body extending from a proximal end to a distal end and having an intermediate portion therebetween. The lead body includes two or more individually insulated conductors, where a first conductor traverses along less than an entire length of the lead body and a second conductor traverses from the proximal end to the distal end of the lead body. Optionally, the first conductor has a different material than the second conductor, for instance having differing electrical properties and/or differing stiffnesses. A method includes varying the stiffness of a coiled conductor assembly including winding a plurality of conductors to form the coiled conductor assembly, and pulling at least one loop of a first conductor away from the coiled conductor assembly.

26 Claims, 8 Drawing Sheets

U.S. PATENT DOCUMENTS

| | | | |
|---|---|---|---|
| 6,083,216 A * | 7/2000 | Fischer, Sr. | 600/374 |
| 6,141,593 A | 10/2000 | Patag | 607/122 |
| 6,178,355 B1 | 1/2001 | Williams et al. | 607/122 |
| 6,188,931 B1 | 2/2001 | Holmstrum et al. | 607/123 |
| 6,249,708 B1 * | 6/2001 | Nelson et al. | 607/122 |
| 6,253,111 B1 * | 6/2001 | Carner | 600/373 |
| 6,400,992 B1 * | 6/2002 | Borgersen et al. | 607/122 |
| 2002/0049485 A1 | 4/2002 | Smits | 607/122 |

FOREIGN PATENT DOCUMENTS

| | | |
|---|---|---|
| EP | 0570710 | 5/1992 |
| WO | 96/06655 | 8/1994 |

* cited by examiner

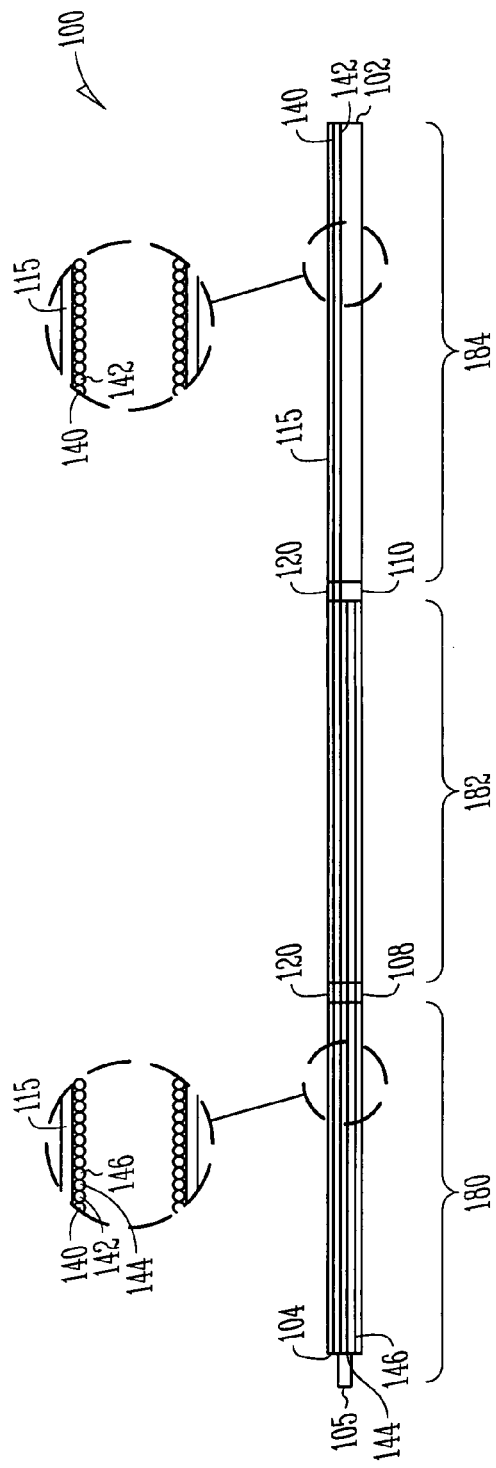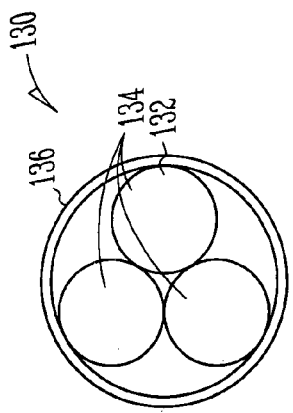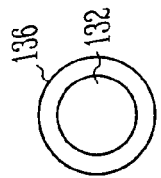

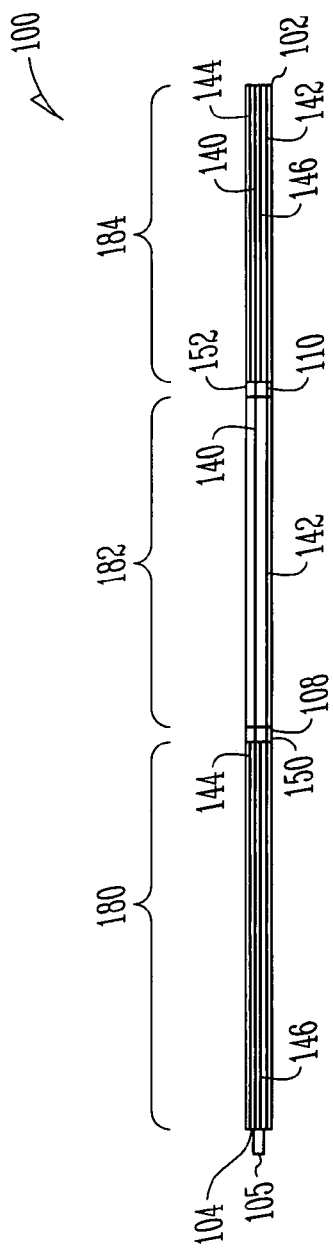
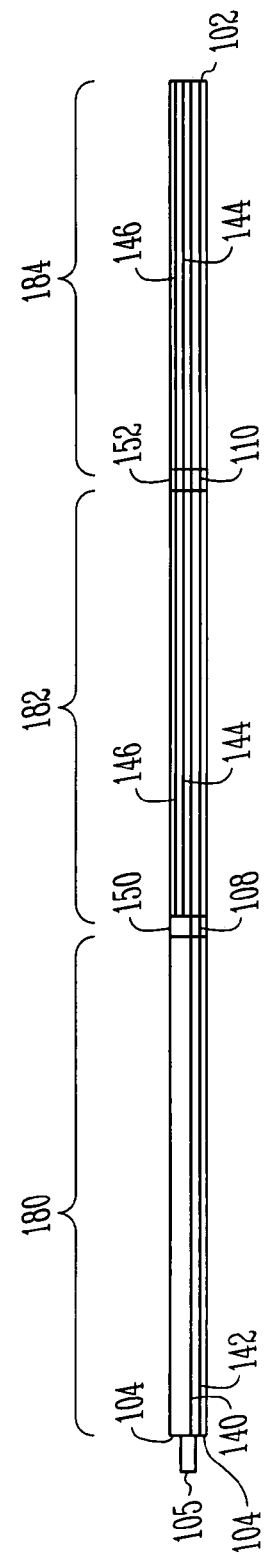
Fig. 3
Fig. 4

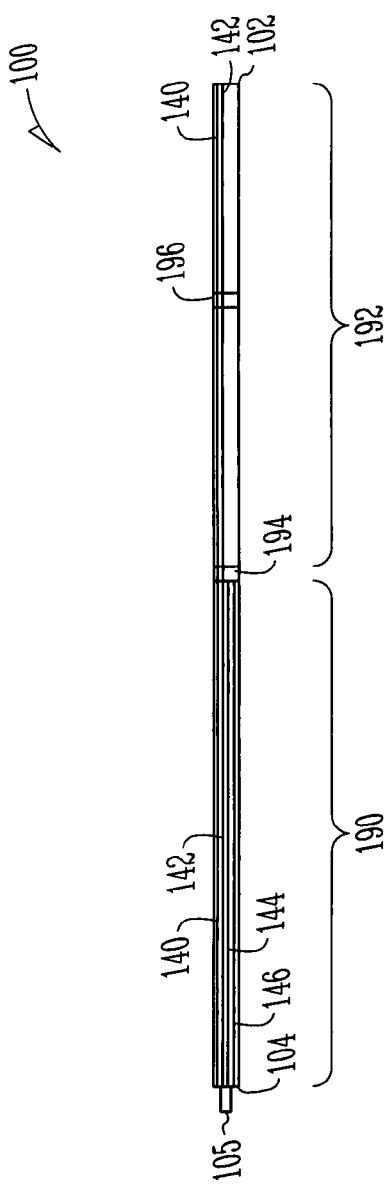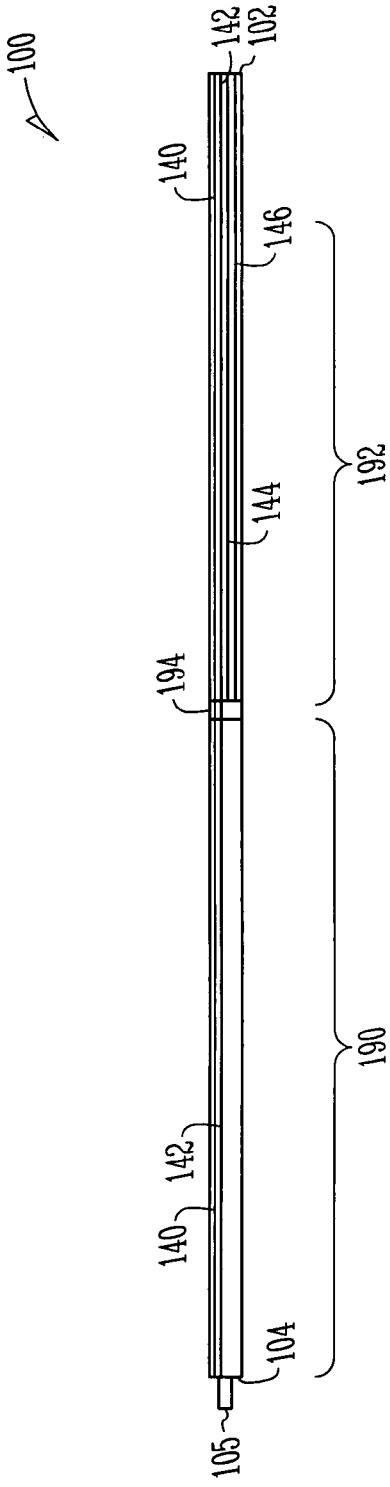

LEAD HAVING VARYING STIFFNESS AND METHOD OF MANUFACTURING THEREOF

TECHNICAL FIELD

The present invention relates generally to leads for conducting electrical signals to and from the heart. More particularly, it pertains to a lead having varying stiffness.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle. Technically, the pacemaker or the automatic implantable cardioverter defibrillator receives signals from the lead and interprets them. The same lead used to sense the condition is sometimes also used in the process of delivering a corrective pulse or signal from the pulse generator of the pacemaker.

Cardiac pacing may be performed by the transvenous method or by leads implanted directly onto the ventricular epicardium. Most commonly, permanent transvenous pacing is performed using a lead positioned within one or more chambers of the heart. The lead may also be positioned in both chambers, depending on the lead, as when a lead passes through the atrium to the ventricle. Electrodes of the lead may be positioned within the atrium or the ventricle of the heart. For other applications, the lead may be positioned in cardiac veins.

Positioning an electrode disposed on a distal end of a lead within a vein presents additional challenges in maintaining the lead in a fixed position since the distal end of the lead does not abut a surface. These challenges also may result in poor pacing and sensing capabilities of the electrode.

Therefore, there is a need for a lead having an electrode for positioning within passages such as cardiac veins, that allows for fixation therein. In addition, what is needed is a lead which can be sufficiently positioned within a patient.

SUMMARY

An apparatus includes a lead body which extends from a proximal end to a distal end and has an intermediate portion therebetween. In addition, the lead body includes two or more individually insulated conductors. At least one of the conductors is a first conductor which traverses along less than an entire length of the lead body. A second conductor traverses from the proximal end to the distal end of the lead body. For instance, the lead body has four conductors disposed at the proximal end of the lead body, and two conductors disposed at the distal end of the lead body. The apparatus further includes an electrode assembly including at least one electrode electrically coupled with at least one of the conductors.

Optionally, the first conductor extends from the distal end of the lead body to the intermediate portion of the lead body. In one embodiment, the first conductor is comprised of a first material, and the second conductor is comprised of a second material, where the first material has a different stiffness and/or electrical property than the second material. Optionally, the first material or the second material comprises conductive polymer material or is formed of material having heat setting capabilities.

In another embodiment, the lead body includes a first section near the distal end, a third section near the proximal end, and a second section disposed between the first and the third sections. The location of the conductors is varied by embodiment. For instance, the first conductor is disposed only in the first and second sections. In another option, the first conductor is disposed only in the first and third sections. In yet another option, the first conductor is disposed only in the second and third sections. For each of these options, a variation includes having the first conductor comprised of material of a greater stiffness than the second conductor. In another embodiment, the electrode is disposed between the second and the third sections.

An apparatus includes a lead body which extends from a proximal end to a distal end and has an intermediate portion therebetween. In addition, the lead body includes two or more individually insulated conductors. At least one of the conductors is a first conductor which is formed of a first material. A second conductor is formed of a second material, which has a different stiffness and/or electrical property than the first material. For instance, the first material comprises MP35N and the second material comprises Pt/Ta.

The apparatus further includes an electrode assembly including at least one electrode electrically coupled with at least one of the conductors. In one embodiment, one of the conductors electrically and mechanically terminates at the electrode assembly. Optionally, the first conductor traverses along less than an entire length of the lead body and the second conductor traverses from the proximal end to the distal end of the lead body.

Further options which can be combined with that above are described below. For instance, one or more conductors includes two or more filars. In another option, the lead body includes a first section near the distal end, a third section near the proximal end, and a second section disposed between the first and the third sections, where the first conductor is disposed in different sections depending on the embodiment. For example, the first conductor is disposed only in the second and third sections, or four conductors are disposed at the proximal end of the lead body, and two conductors are disposed at the distal end of the lead body.

A method includes varying the stiffness of a coiled conductor assembly including winding a plurality of conductors to form the coiled conductor assembly, and pulling at least one loop of a first conductor away from the coiled conductor assembly. In addition, the method optionally includes crimping the at least one loop and/or electrically coupling the first conductor to an electrode. Optionally, the first conductor is electrically terminated at the electrode. Additional optional steps includes spinning a mandrel and forming the coiled conductor assembly therein, and pulling the loop includes stopping the mandrel. One or more second loops of a second conductor are also pulled, wherein pulling one or more second loops of a second conductor involves pulling a second conductor having a different material than the first conductor.

A method includes modifying a stiffness of a lead extending from a proximal end to a distal end, where the lead includes two or more conductors. Modifying the stiffness includes forming insulation on the two or more conductors, winding the two or more conductors and dropping out one or more conductors at an intermediate portion of the lead. Optionally, winding the two or more conductors includes winding two or more conductors each having a different material. An additional optional step includes pulling a loop of at least one conductor during the winding. The method further includes, in another embodiment, crimping and swaging the loop of conductor. Optionally, the method further includes electrically coupling the conductor with an electrode of the lead.

The lead assembly provides several benefits including a lead which has varying stiffness throughout the lead. Furthermore, the conductors and/or portions of the lead formed of materials having increased stiffness will assist in retaining and/or positioning the lead assembly in a desired location of the heart or vein or artery. The lead assembly is also beneficial in applications where the electrode is disposed in a larger vein or artery where it is otherwise difficult to position and/or maintain an electrode against the wall of the surrounding tissue.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1 is a cross-section view illustrating a lead assembly constructed in accordance with one embodiment.

FIG. 2A is a cross-section view illustrating a conductor constructed in accordance with one embodiment.

FIG. 2B is a cross-section view illustrating a conductor constructed in accordance with one embodiment.

FIG. 3 is a cross-section view illustrating a lead assembly constructed in accordance with one embodiment.

FIG. 4 is a cross-section view illustrating a lead assembly constructed in accordance with one embodiment.

FIG. 5 is a cross-section view illustrating a lead assembly constructed in accordance with one embodiment.

FIG. 6 is a cross-section view illustrating a lead assembly constructed in accordance with one embodiment.

DETAILED DESCRIPTION

Figure 7:
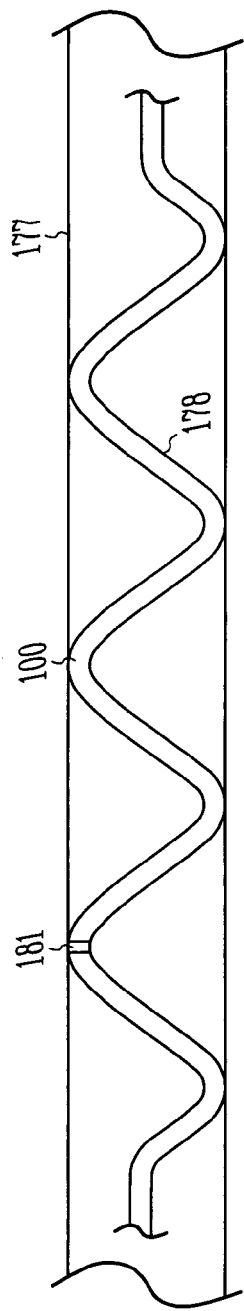
FIG. 7 is an elevational view illustrating a lead assembly constructed in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIG. 1 illustrates a lead 100 for delivering electrical pulses to stimulate a heart and/or for receiving electrical pulses to monitor the heart. The lead 100 includes a lead body 1115 which is covered by a biocompatible insulating material. Silicone rubber or other insulating material is used for covering the lead body 115. The lead 100 has a distal end 102 adapted for implant within a body, for instance within a vein, and a proximal end 104. The proximal end 104 has a connector terminal 105 which electrically connects the various electrodes and conductors within the lead 100 to a pulse generator and signal sensor. The terminal connector 105 provides for the electrical connection between the lead 100 and the pulse generator. The pulse generator contains electronics to sense various electrical signals of the heart and also to produce current pulses for delivery to the heart.

Disposed between the distal end 102 and the proximal end 104 of the lead 100 is an intermediate portion, as will be further described below. The lead 100 includes at least one electrode 120 disposed between the distal end 102 and the proximal end 104. At least one conductor 130 (FIG. 2) is electrically coupled with the at least one electrode 120. The at least one conductor 130 comprises a coiled conductor 130 which includes one or more filars 132. FIG. 2A illustrates the at least one conductor 130 with one filar 132. In one embodiment, as shown in FIG. 2B, the at least one conductor 130 has three filars 134. Other options include a conductor which is a solid wire, or a conductor which has braided strands of wire or filars. The at least one conductor 130 includes insulation 136 thereover. Suitable materials for insulation include, but are not limited to, ETFE, silicone, polyurethane, or other insulating material. Optionally, the lead 100 includes two or more conductors 130. It should be noted, however, that each conductor 130 need not be electrically coupled with the at least one electrode 120.

Referring again to FIG. 1, the lead 100 is defined in part by a first intermediate portion 108 and a second intermediate portion 110. The first intermediate portion 108 is more near the proximal end 104 of the lead 100 than the second intermediate portion 110, such that the lead 100 is defined by multiple sections. A first section 180 is disposed between the proximal end 104 and the first intermediate portion 108, a second section 182 is disposed between the first intermediate portion 108 and the second intermediate portion 110. A third section 184 of the lead 100 is disposed between the second intermediate portion 110 and the distal end 102.

A first conductor 140 and a second conductor 142 extend from the proximal end 104 to the distal end 102 of the lead 100. A third conductor 144 and a fourth conductor 146 extend from the proximal end 104 to the second intermediate portion 110. As a result, the first and second conductors 140, 142 are disposed in the first, second, and third sections 180, 182, 184 of the lead 100. The third and fourth conductors 144, 146 are disposed in the first and second sections, 180, 182. Optionally, an electrode 120 is disposed between the first and second sections 180, 182, and/or the electrode 120 is disposed between the second and third sections 182, 184. One or more of the first, second, third, or fourth conductors 140, 142, 144, 146 optionally electrically terminate at the electrode 120. As shown in FIG. 1, the first, second, third, and fourth conductors 140, 142, 144, 146 are coradial, in one option. For instance, the first, second, third, and fourth conductors 240, 242, 244, 246 extend around a single axis (e.g. the longitudinal axis of the lead 100) and have substantially similar radii with respect to the single axis.

FIG. 3 illustrates an alternative for the lead 100, where the first conductor 140 and the second conductor 142 extend from the proximal end 104 to the distal end 102 of the lead 100. The third conductor 144 extends from a second intermediate portion 110 to the distal end 102 of the lead 100. Optionally, the third conductor 144 extends from the proximal end 104 to a first intermediate portion 108, terminating at the first intermediate portion 108. In another alternative, a fourth conductor 146 extends from the second intermediate portion 110 to the distal end 102 of the lead 100, and extends from the proximal end 104 to the first intermediate portion 108. As a result, the first and second conductors are disposed in the first, second, and third sections 180, 182, 184 of the lead 100. The third and fourth conductors 144, 146 are disposed in the first and third sections, 180, 184. Optionally, a first electrode 150 is disposed between the first and second sections 180, 182 where third and fourth conductors 144, 146 mechanically and electrically terminate at the first electrode 150. In another option, a second electrode 152 is disposed between the second and third sections 182, 184, and the third and fourth conductors 144, 146 mechanically and electrically terminate at the second electrode 152.

FIG. 4 illustrates another alternative for the lead 100, where the first conductor 140 and the second conductor 142 extend from the proximal end 104 to the distal end 102 of the lead 100. The third conductor 144 and the fourth conductor 146 extend from the first intermediate portion 108 to the distal end 102 of the lead 100. As a result, the first and second conductors are disposed in the first, second, and third sections 180, 182, 184 of the lead 100. The third and fourth conductors 144, 146 are disposed in the second and third sections, 182, 184. Optionally, the first electrode 150 is disposed between the first and second sections 180, 182 where third and fourth conductors mechanically terminate at the first electrode 150. In another option, a second electrode 152 is disposed between the second and third sections 182, 184, where the third and fourth conductors 144, 146 optionally electrically terminate at the second electrode.

Referring to FIG. 5, another alternative of the lead 100 is shown which is defined in part by a first section 190 and a second section 192. The first section 190 is more near the proximal end 104 of the lead 100 than the second section 192 such that the lead 100 is defined by multiple sections. Optionally, the lead 100 includes a first electrode 194 and/or a second electrode 196, where the first electrode 194 is disposed between the first section 190 and the second section 192, and the second electrode 196 is disposed in the second section 192.

A first conductor 140 and a second conductor 142 extend from the proximal end 104 to the distal end 102 of the lead 100. A third conductor 144 and a fourth conductor 146 extend along the first section 190. The third conductor 144 and the fourth conductor 146 electrically and mechanically terminate at the optional first electrode 194. As a result, the first and second conductors 140, 142 are disposed in the first and second sections 190, 192 of the lead 100. The third and fourth conductors 144, 146 are disposed in the first section 190 of the lead 100.

FIG. 6 illustrates another alternative of the lead 100. A first conductor 140 and a second conductor 142 extend from the proximal end 104 to the distal end 102 of the lead 100. A third conductor 144 and a fourth conductor 146 extend along only the second section 192. The third conductor 144 and the fourth conductor 146 electrically and mechanically terminate at the optional first electrode 194. As a result, the first and second conductors 140, 142 are disposed in the first and second sections 190, 192 of the lead 100. The third and fourth conductors 144, 146 are disposed only in the first section 190 of the lead 100.

Figure 15:
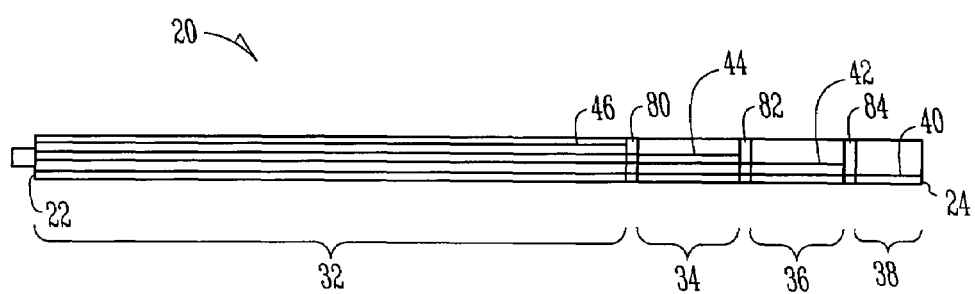
FIG. 15 is a cross-section view illustrating a lead assembly constructed in accordance with one embodiment.
Figure 16:
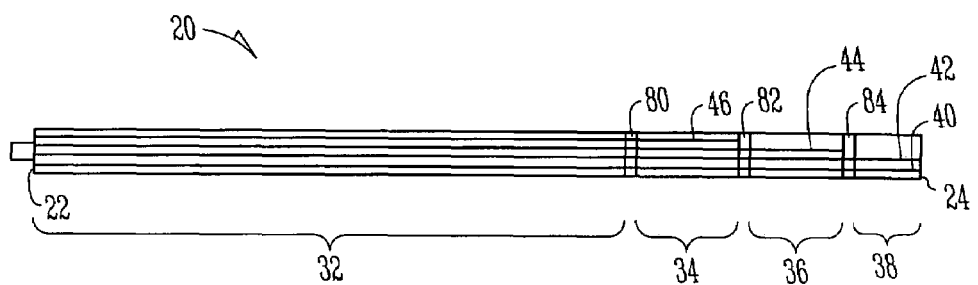
FIG. 16 is a cross-section view illustrating a lead assembly constructed in accordance with one embodiment.

FIGS. 15 and 16 illustrate other options for a lead 20. Similar to that above, the lead 20 extends from a proximal end 22 to a distal end 24. The lead 20 includes four sections 32, 34, 36, 38, where the fourth section 38 is adjacent to the distal end 24. Optionally disposed between the sections is one or more electrodes. For instance, a first electrode 80 is disposed between the first section 32 and the second section 34, a second electrode 82 is disposed between the second section 34 and the third section 36, and a third electrode 84 is disposed between the third section 36 and the fourth section 38. It is possible to have more electrodes or fewer electrodes than the first, second, and third electrodes 80, 82, 84.

Referring to FIG. 15, a first conductor 40 extends from the proximal end 22 to the distal end 24 of the lead 20. A second conductor 42 extends from the proximal end 22 to the third electrode 84. A third conductor 44 extends from the proximal end 22 to the second electrode 82. A fourth conductor 46 extends from the proximal end 22 to the first electrode 80. Optionally, instead of any of the above mentioned electrodes, the conductors merely terminate at a location of the electrode, and the electrode is not included.

Referring to FIG. 16, the first and second conductors 40, 42 extend from the proximal end 22 to the distal end 24 of the lead 20. The third conductor 44 extends from the proximal end 22 to the third electrode 84. The fourth conductor 46 extends from the proximal end 22 to the second electrode 82. Optionally, instead of any of the above mentioned electrodes, the conductors merely terminate at a location of the electrode, and the electrode is not included.

The conductors are formed, in one example, by winding. The materials used for each conductor are optionally varied, such that the stiffness of the material and the conductor are varied. For instance, of the above discussed lead 100, the first conductor 140 and the second conductor 142 are formed of a first material and the third conductor 144 and the fourth conductor 146 are formed of a second material. Optionally, the first material has a different stiffness than the second material. Examples of materials which are used to form any of the conductors include, but are not limited to, MP35N, Pt/Ir composites, which are relatively stiff materials. Less stiff materials include a composite of MP35N with a Ta core or a composite of MP35N with a Ag core. Relatively lesser stiff materials are also used including, but not limited to, Pt clad Ta, Pt clad Ti, or Ti. In another alternative, a conductive polymer is used to form the conductor.

In another option, materials having different electrical properties are used to form the conductors. For instance, at least one conductor is formed of a material having a first electrical property, and at least another conductor is formed of a material having a second electrical property. Having conductors formed of two different materials of differing electrical properties results in electrodes of the lead 100 to exhibit different electrical properties, for example, impedance. In yet another option, a material having heat setting properties is used to form one or more of the conductors of the lead 100 such that desired shapes for fixation and electrode contact can be achieved. It should be noted that any of the above discussed materials can be used in any of the above and below discussed embodiments. Other materials which will affect the properties of the lead 100 can also be used.

Figure 8:
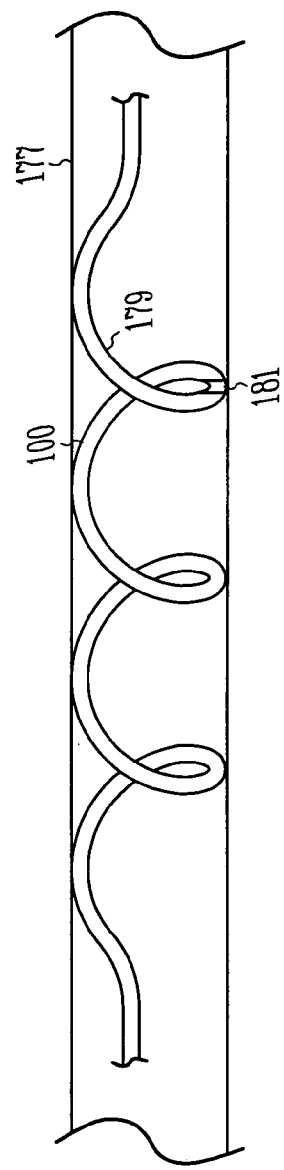
FIG. 8 is an elevational view illustrating a lead assembly constructed in accordance with one embodiment.

As an example of using different materials, the lead includes two conductors which extend the entire length of the lead, and are formed of Pt/Ta. Two other conductors extend less than the entire length of the lead and are formed of MP35N, which is more stiff than the Pt/Ta. The less stiff material which extends to the distal end 102 of the lead 100 allows for suitable flexibility for chronic placement of the lead 100 within a vein of a patient. In addition, the material also provides a gentle bias in the area of the electrode such that sufficient force is provided for tissue contact by the electrode. For instance, as shown in FIGS. 7 and 8, the lead 100 and the coiled conductors therein is formed into a shape having a two 178 or three 179 dimensional bias. The lead 100 having a bias allows for tissue contact between an electrode 181 and a wall of a vein 177. It should be noted that the lead 100 is not limited to having four conductors and the number of conductors and the materials used for each can be modified.

Figure 9:
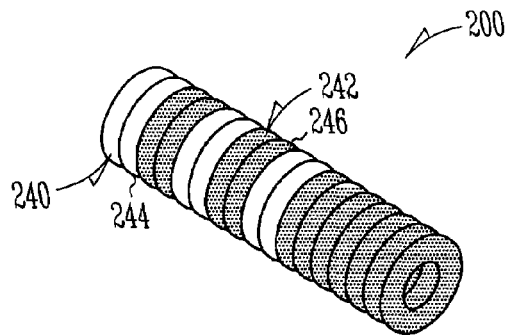
FIG. 9 is a perspective view illustrating a portion of a conductor assembly constructed in accordance with one embodiment.

As discussed above, the lead 100 includes a first conductor and a second conductor, which, in one embodiment, are formed of two different materials. FIG. 9 illustrates one example of a winding configuration for a portion of a conductor assembly 200 for use in the lead 100 which includes a first conductor 240 and a second conductor 242 each formed of a different material. Optionally, a third 244 and a fourth 246 conductor are included. For instance, the first conductor 240 and the third conductor 244 are formed of MP35N and the second 242 and the fourth 246 conductor are formed of Pt/Ta. As shown in FIG. 9, in another option, the first, second, third, and fourth conductors 240, 242, 244, 246 are coradial. For example, the conductors 240, 242, 244, 246 are wound around a single axis (e.g. the longitudinal axis of the lead 100) and have substantially similar radii with respect to the single axis. The first conductor 240, second conductor 242, third conductor 244, and fourth conductor 246 are each wound together, and transition to the second conductor 242 and the fourth conductor 246, as shown in FIG. 9, and as further described below. It should be noted that the conductor assembly 200 can be used in any of the above or below described embodiments, and that other winding configurations are possible.

Figure 10:
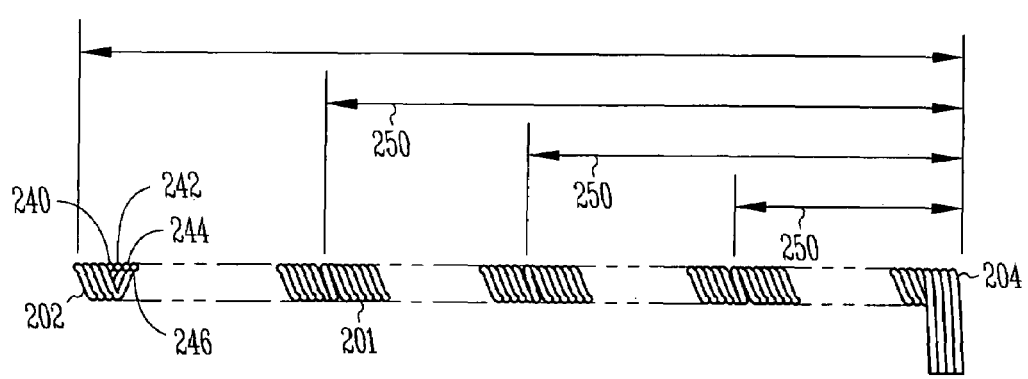
FIG. 10 is an elevational view illustrating a portion of a conductor assembly constructed in accordance with one embodiment.

FIG. 10 illustrates another example of how to form the conductor assembly 200. The conductor assembly 200 is wound, for example, using a mandrel. The conductor assembly 200 is wound with four conductors, including the first conductor 240, second conductor 242, third conductor 244, and fourth conductor 246, which are each wound from a proximal end 204 to a distal end 202 of the conductor assembly 200. As shown in FIG. 10, in one option, the first, second, third, and fourth conductors 240, 242, 244, 246 are coradial, as described above. In one embodiment, two or more different materials are used for forming the conductor assembly 200. In another embodiment, one or more of the first conductor 240, second conductor 242, third conductor 244, and fourth conductor 246 are electrically terminated at various locations 250 along the conductor assembly 200. Optionally, during the winding of the coil assembly 200, one or more of the first conductor 240, second conductor 242, third conductor 244, and fourth conductor 246 is dropped out of the winding, for instance, at a location of an electrode.

Figure 11:
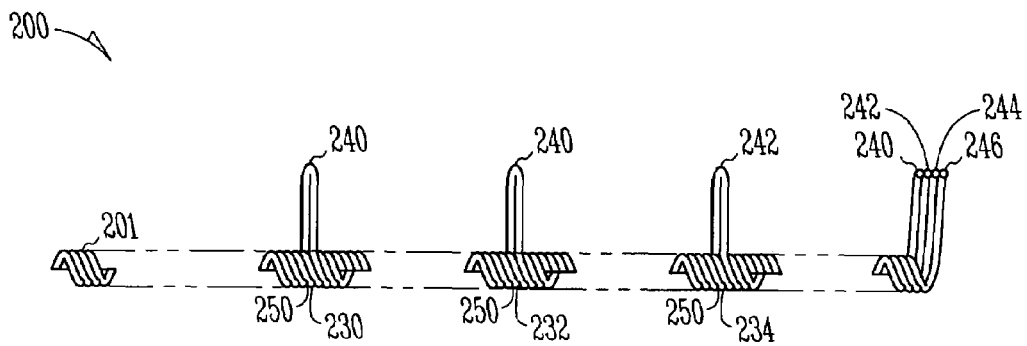
FIG. 11 is an elevational view illustrating a portion of a conductor assembly constructed in accordance with one embodiment.

FIG. 11 illustrates another example of how to form the conductor assembly 200. The conductor assembly 200 is wound, for example, using a mandrel. The conductor assembly 200 is wound with four individually insulated conductors, including the first conductor 240, second conductor 242, third conductor 244, and fourth conductor 246. In one embodiment, two or more different conductor materials are used for forming the conductor assembly 200. During the winding process, one or more of the first conductor 240, second conductor 242, third conductor 244, and fourth conductor 246 are pulled out of the winding. For example, at a first location 230, the first conductor 240 is pulled from the coil 201, and yet the first conductor 240 continues being wound past the first location 230. The first conductor 240 is pulled from the coil 201 at a second location 232, and the first conductor 240 continues being wound past the second location 232. At a third location 234, the second conductor 242 is pulled from the coil 201 and the second conductor 242 continues being wound past the third location 234. Rather than terminating the filars, the conductors are reintroduced into the winding, either to another location of the coil assembly 200, such as at an electrode, or to the distal end of the coil assembly.

Optionally, one or more of the first conductor 240, second conductor 242, third conductor 244, and fourth conductor 246 are electrically terminated at various locations 250 along the conductor assembly. Advantageously, pulling the loop allows for the conductor to be electrically coupled with the electrode, but yet optionally allows the electrical connection to be thereafter terminated as the conductor extends to the distal end of the lead 100. Another benefit provided is that a single conductor can be coupled with more than one electrode, providing more options for the lead designer and the physician.

Figure 12:
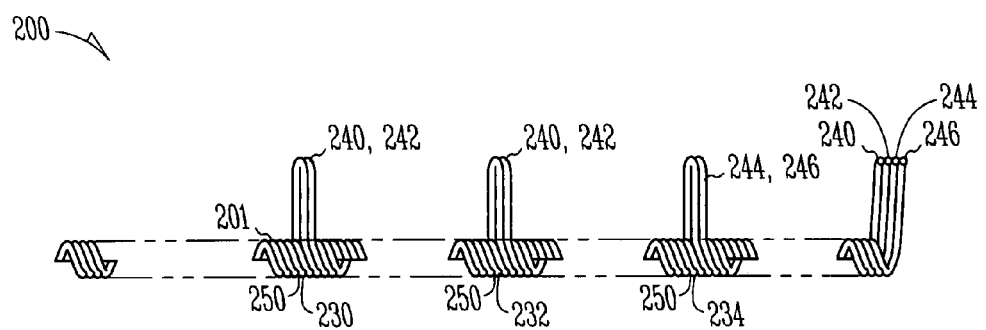
FIG. 12 is an elevational view illustrating a portion of a conductor assembly constructed in accordance with one embodiment.

FIG. 12 illustrates another example of how to form the conductor assembly 200. The conductor assembly 200 is wound, for example, using a mandrel. The conductor assembly 200 is wound with, for example, four conductors, including the first conductor 240, second conductor 242, third conductor 244, and fourth conductor 246 to form the coil 201. It should be noted that in this and the above and below discussed embodiments, the number of conductors can be changed, yet are considered within the scope of the application. In one embodiment, two or more different materials are used for forming the conductor assembly 200.

During the winding process, two or more of the first conductor 240, second conductor 242, third conductor 244, and fourth conductor 246 are pulled out of the winding. The mandrel is optionally stopped while the conductors are pulled out of the winding, and then restarted to continue the winding process. For example, at a first location 230, the first conductor 240 and the second conductor 242 are each pulled from the coil 201, and yet the first conductor 240 and/or the second conductor 242 continues being wound past the first location 230. The second conductor 242 is pulled at the same location as the first conductor 240, such that the second conductor 242 is adjacent to the first conductor 240. The first conductor 240 and the second conductor 242 are pulled from the coil 201 at a second location 232, and the first conductor 240 and/or the second conductor 242 continues being wound past the second location 232.

At a third location 234, the third conductor 244 and the fourth conductor 246 are pulled from the coil 201 and the third conductor 244 and/or the fourth conductor 246 continues being wound past the third location 234. Rather than mechanically terminating the filars, the conductors are reintroduced into the winding, either to another location of the coil assembly 200, such as at an electrode, or to the distal end of the coil assembly. Optionally, one or more of the first conductor 240, second conductor 242, third conductor 244, and fourth conductor 246 are electrically terminated at various locations 250 along the conductor assembly.

Figure 13:
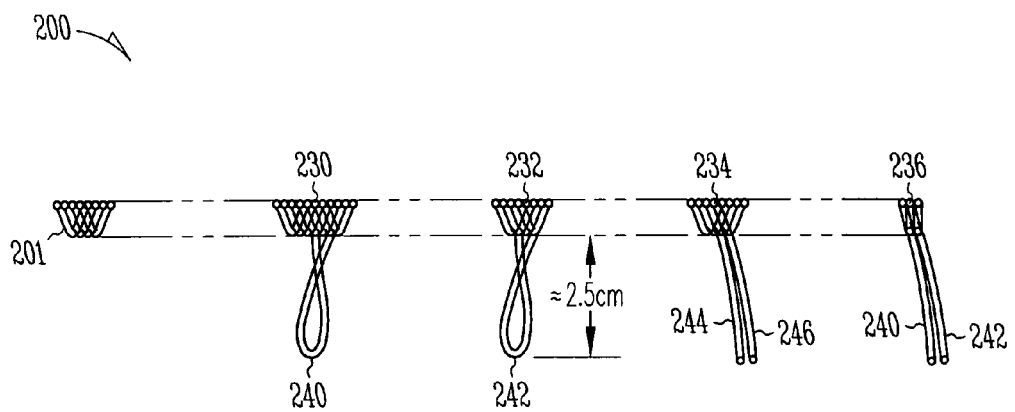
FIG. 13 is an elevational view illustrating a portion of a conductor assembly constructed in accordance with one embodiment.

FIG. 13 illustrates another example of how to form the conductor assembly 200. The conductor assembly 200 is wound, for example, using a mandrel. The conductor assembly 200 is wound with, for example, four conductors, including the first conductor 240, second conductor 242, third conductor 244, and fourth conductor 246 to form the coil 201. In one embodiment, two or more different materials are used for forming the conductor assembly 200.

During the winding process, one or more of the first conductor 240, second conductor 242, third conductor 244, and fourth conductor 246 are pulled out of the winding at one or more locations, and two or more of the first conductor 240, second conductor 242, third conductor 244, and fourth conductor 246 are pulled out of the winding at one or more locations. To pull the conductors, the mandrel is optionally stopped while the conductors are pulled out of the winding, and then restarted to continue the winding process.

At a first location 230, for example, the first conductor 240 is pulled from the coil 201, and yet the first conductor 240 continues being wound past the first location 230. At a second location 232, the second conductor 242 is pulled from the coil 201, and yet the second conductor 242 continues being wound past the second location 232. At a third location 234, the third conductor 244 and the fourth conductor 246 are pulled from the coil 201 and the third conductor 244 and/or the fourth conductor 246 continues being wound past the third location 234. The first conductor 240 and the second conductor 242 are pulled from the coil 201 at a fourth location 236, and the first conductor 240 and/or the second conductor 242 continues being wound past the fourth location 236. The second conductor 242 is pulled at the same location as the first conductor 240, such that the second conductor 242 is adjacent to the first conductor 240.

For any of the conductors, rather than mechanically terminating the filars, the conductors are optionally reintroduced into the winding, either to another location of the coil assembly 200, such as at an electrode, or to the distal end of the coil assembly. Optionally, one or more of the first conductor 240, second conductor 242, third conductor 244, and fourth conductor 246 are electrically terminated at various locations along the conductor assembly.

Figure 14:
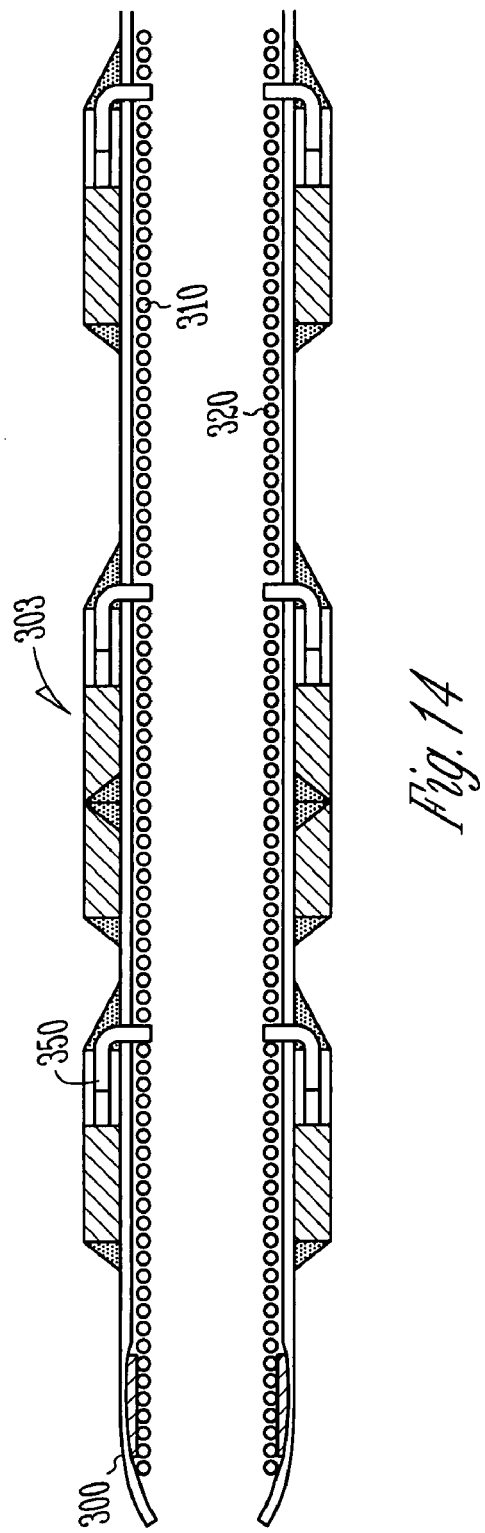
FIG. 14 is a cross-section view illustrating a portion of a lead assembly constructed in accordance with one embodiment.

FIG. 14 illustrates a lead 300 with a conductor assembly 320. The conductor assembly 320 includes, but is not limited to, those which are formed with the above methods, or above discussed structures. The conductor assembly 320 includes one or more conductors 310. One or more of the conductors 310 is electrically coupled with at least one electrode 350. Optionally, one or more of the conductors is mechanically and/or electrically terminated at an intermediate portion 303 of the lead 300. For example, a conductor is pulled during the winding process. The conductor is then crimped, swaged, welded or otherwise mechanically and electrically coupled with the electrode 350. It should be noted that other methods, or combinations of methods, of mechanically and/or electrically coupling the conductor with the electrode 350 would be suitable as well.

The above-described lead assembly provides several benefits including a lead which has varying stiffness throughout the lead. Furthermore, the conductors and/or portions of the lead formed of materials having increased stiffness will assist in retaining and/or positioning the lead assembly in a desired location of the heart or vein or artery. The lead assembly is also beneficial in applications where the electrode is disposed in a larger vein or artery where it is otherwise difficult to position and/or maintain an electrode against the wall of the surrounding tissue.

It is to be understood that the above description is intended to be illustrative, and not restrictive. Although the use of the lead has been described for use in a cardiac pacing system, the lead could be applied to other types of body stimulating systems or the embodiments could be used in the application of other medical devices. Furthermore, it should be noted that the above described embodiments include windings which are right hand wound, and windings which are left hand wound. Many other embodiments and applications will be apparent to those of skill in the art upon reviewing the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An apparatus comprising:
    a lead body extending from a proximal end to a distal end and having an intermediate portion therebetween, the lead body including two or more coradial individually insulated coradial conductors disposed therein, wherein the coradial conductors are wound about a single axis, at least one of the individually insulated coradial conductors is formed of material having heat setting capabilities;
    the individually insulated coradial conductors including a first conductor and a second conductor, the first conductor comprised of a first material, and the second conductor comprised of a second material, wherein the first material has a different stiffness than the second material; and
    an electrode assembly including at least one electrode electrically coupled with at least one of the conductors.

2. The apparatus as recited in claim 1, wherein at least one coradial conductor traverses from the proximal end to the distal end, and at least one other coradial conductor traverses along only a portion of the lead body.

3. The apparatus as recited in claim 2, wherein the at least one other coradial conductor electrically and mechanically terminates at the electrode assembly.

4. The apparatus as recited in claim 1, wherein one or more coradial conductors includes two or more filars.

5. The apparatus as recited in claim 1, wherein the first material and the second material have different electrical properties.

6. The apparatus as recited in claim 1, wherein the first material comprises MP35N.

7. The apparatus as recited in claim 6, wherein the second material comprises Pt/Ta.

8. The apparatus as recited in claim 7, wherein the lead body includes a first section near the distal end, a third section near the proximal end, and a second section disposed between the first and the third sections, where the first coradial conductor is disposed only in the second and third sections.

9. The apparatus as recited in claim 1, wherein the individually insulated coradial conductors further include a third coradial conductor and a fourth coradial conductor, the first, second, third, and fourth conductors disposed at the proximal end of the lead body, and the first and second conductors disposed at the distal end of the lead body.

10. The apparatus as recited in claim 1, wherein the individually insulated coradial conductors and the lead body have a two or three dimensional bias.

11. The apparatus as recited in claim 1, wherein the coradial conductors form a single lumen within the lead body.

12. The apparatus recited in claim 1, wherein the lead body includes a first section near the distal end, a third section near the proximal end, and a second section disposed between the first and third sections, where the first conductor is disposed only in the first and third sections.

13. The apparatus recited in claim 1, wherein the two or more coradial conductors are concentric with the lead body.

14. The apparatus recited in claim 1, wherein the two or more coradial conductors lie adjacent to the outer surface of the lead body.

15. The apparatus recited in claim 1, wherein the individually insulated coradial conductors include a first individually insulated coradial conductor and a second individually insulated coradial conductor, the first individually insulated coradial conductor including the first material, and the second individually insulated coradial conductor including the second material.

16. The apparatus recited in claim 1, wherein at least the first conductor extends from the distal end of the lead body to the intermediate portion.

17. The apparatus recited in claim 1, wherein the first material or the second material comprises conductive polymer material.

18. The apparatus recited in claim 1, wherein the lead body includes a first section near the distal end, a third section near the proximal end, and a second section disposed between the first and the third sections, where the first conductor is disposed only in the second and third sections.

19. The apparatus recited in claim 18, wherein the first conductor is comprised of material having a greater stiffness than the second conductor.

20. The apparatus recited in claim 18, wherein the at least one electrode is disposed between the second and third sections.

21. The apparatus recited in claim 1, wherein at least one individually insulated coradial conductor includes at least one conductor loop pulled away from a portion of the at least one individually insulated coradial conductor.

22. The apparatus recited in claim 21, wherein the at least one conductor loop includes a crimped conductor loop along the lead body.

23. The apparatus recited in claim 22, wherein the at least one electrode is coupled over the crimped conductor loop.

24. The apparatus recited in claim 21, wherein the at least one conductor loop includes the conductor loop swaged along the lead body.

25. The apparatus recited in claim 21, wherein a second individually insulated coradial conductor includes a second conductor loop pulled away from a second portion of the second individually insulated coradial conductor.

26. The apparatus recited in claim 25, wherein the first conductor loop is adjacent to the second conductor loop.

* * * * *

UNITED STATES PATENT AND TRADEMARK OFFICE
CERTIFICATE OF CORRECTION

| | |
|---|---|
| PATENT NO. | : 7,239,923 B1 |
| APPLICATION NO. | : 09/630000 |
| DATED | : July 3, 2007 |
| INVENTOR(S) | : Tockman et al. |

It is certified that error appears in the above-identified patent and that said Letters Patent is hereby corrected as shown below:

On the Title page, in field (56), under "U.S. Patent Documents", in column 2, line 1, delete "Martynink" and insert -- Martyniuk --, therefor.

Signed and Sealed this

Ninth Day of October, 2007

JON W. DUDAS
*Director of the United States Patent and Trademark Office*